United States Patent [19]
Hickey

[11] Patent Number: 5,921,935
[45] Date of Patent: *Jul. 13, 1999

[54] METHOD AND APPARATUS UTILIZING HEART SOUNDS FOR DETERMINING PRESSURES ASSOCIATED WITH THE LEFT ATRIUM

[75] Inventor: Donald D. Hickey, Amherst, N.Y.

[73] Assignee: The Research Foundation of State University of New York, Buffalo, N.Y.

[*] Notice: This patent is subject to a terminal disclaimer.

[21] Appl. No.: 08/920,129

[22] Filed: Sep. 2, 1997

Related U.S. Application Data

[60] Division of application No. 08/377,466, Jan. 24, 1995, Pat. No. 5,697,375, which is a continuation-in-part of application No. 08/114,775, Aug. 31, 1993, Pat. No. 5,398,692, which is a continuation of application No. 07/980,460, Nov. 23, 1992, Pat. No. 5,263,485, which is a continuation-in-part of application No. 07/717,854, Jun. 25, 1991, Pat. No. 5,181,517, which is a continuation-in-part of application No. 07/409,041, Sep. 18, 1989, Pat. No. 5,048,532.

[51] Int. Cl.$^6$ ........................................................ A61B 5/00
[52] U.S. Cl. ........................... 600/485; 600/500; 600/561; 600/587; 600/593
[58] Field of Search ...................... 600/587, 593, 600/561, 488, 485, 486, 500

[56] References Cited

U.S. PATENT DOCUMENTS

| | | | |
|---|---|---|---|
| 4,134,402 | 1/1979 | Mahurkar | 128/214 |
| 4,214,593 | 7/1980 | Imbruce et al. | 128/748 |
| 4,379,460 | 4/1983 | Judell | 128/671 |
| 4,409,986 | 10/1983 | Apple et al. | 128/715 |
| 4,502,490 | 3/1985 | Evans et al. | 128/780 |
| 4,517,984 | 5/1985 | Perlin | 128/642 |
| 4,706,688 | 11/1987 | Don Micheal et al. | 128/785 |
| 4,729,384 | 3/1988 | Bazenet | 128/691 |
| 4,850,969 | 7/1989 | Jackson | 604/96 |
| 5,048,532 | 9/1991 | Hickey | 128/780 |
| 5,181,517 | 1/1993 | Hickey | 128/673 |
| 5,191,892 | 3/1993 | Blikken | 128/715 |
| 5,263,485 | 11/1993 | Hickey | 128/673 |
| 5,269,775 | 12/1993 | Bodickey | 604/96 |
| 5,398,692 | 3/1995 | Hickey | 128/673 |
| 5,433,216 | 7/1995 | Sugrue et al. | 128/780 |
| 5,570,671 | 11/1996 | Hickey | 600/486 |
| 5,697,375 | 12/1997 | Hickey . | |

FOREIGN PATENT DOCUMENTS

| | | | |
|---|---|---|---|
| 1069826 | 9/1982 | U.S.S.R. | 604/96 |

OTHER PUBLICATIONS

"We'll meet your needs.", Teleflex Medical/Fluoroplastics, Incorporated, Tall Pines Park, Jaffrey NH 03452.

Brown, A Study of the Esophageal Lead in Clinical Electrocardiography, American Heart J., vol. 12, No. 1, Jul., 1936, pp. 1–45.

(List continued on next page.)

*Primary Examiner*—Robert L. Nasser
*Attorney, Agent, or Firm*—James C. Simmons

[57] ABSTRACT

Non-invasive apparatus and method for obtaining a quantitative determination of mean left atrial transmural pressure or otherwise obtaining a quantitative determination of a left atrial pressure value. A balloon is inserted by means of a catheter into the esophagus and positioned adjacent the left atrium. The balloon is gradually inflated. A tracing of mean balloon pressure is obtained as the balloon is inflated. In addition, a tracing of balloon pressure on a steady baseline and with low frequency oscillations due to respiration filtered out is obtained whereby the tracing represents balloon pressure oscillations effected by left atrial pressure. In accordance with the oscillometric principle the mean balloon pressure is measured when the intensity of a sound wave, after its transmission through the balloon, is at a peak. This mean balloon pressure, after adjustment for the effect, if any, of heart weight, is indicative of approximate mean left atrial pressure. Mean left atrial transmural pressure may be determined by adjusting for the effects of heart weight and intrapleural pressure on mean pressure at peak sound intensity by subtracting therefrom the balloon pressure at which balloon volume begins to increase greatly relative to the increase in balloon pressure.

6 Claims, 7 Drawing Sheets

OTHER PUBLICATIONS

Oblath and Karpman, The Normal Esophageal Lead Electrocardiogram American Heart J., vol. 41, 1951, pp. 369–381.

Arborelius et al, Hemodynamic Changes in Man During Immersion with Head Above Water, Aerospace Medicine, Jun., 1972, pp. 592–598.

Lategola and Rahn, A Self–Guiding Catheter for Cardiac and Pulmonary Arteria Catheterization and Occlusion, 84 Proc. Soc. Exp. Biol. Med. 667–668 (1953).

Swan, Ganz, Forrester, Marcus, Diamond and Chonette, Catheterization of the Heart in Man With Use of a Flow–Directed Balloon–Tipped Catheter, 283:9 The New England J. Med. 447 (1970).

Murray, Complications of Invasive Monitoring, 15:2 Medical Instrumentation 85 at P. 89 (Mar.–Apr. 1981).

Robin, Death by Pulmonary Artery Flow–Directed Catheter (editorial), time for a Moratorium?, 92:4 Chest 727 (Oct. 1987).

H.R. Anderson and P. Pless, Trans–Esophageal Pacing, 6 PACE 674 (Jul.–Aug. 1983).

R.P. Lasser and L. Loewe, Characteristic Pressure Pulses Recorde with an Esophageal Balloon in Experimental Mitral Insufficiency Dogs, Proc. Soc. Experimental Biol. Med. 77:798 (1951).

R.P. Lasser and L. Loewe, Esophageal Pressure Pulse Patterns (Esophageal Piezocardiogram), Am. Heart J. 44:531 (1952).

A.C. Taquini, The Esophageal Pulse Under Normal and Abnormal Conditions, Am. Heart J. 20:2 (1940).

M. Zoob, The Esophageal Pulse in Mitral Valve Disease, Brit. Heart J. 16:39 (1954).

A. J. Gordon, L. Kuhn S. S. Amram, E. Donoso, E. Braunwald, Left Atrial, "Pulmonary Capillary," and Esophageal Balloon Pressure Tracings in Mitral Valve Disease, Brit. Heart J. 18:327–340 (1956).

Robin, The Cult of the Swan–Ganz Catheter, Overuse and Abuse of Pulmonary Flow Catheters, 103:3 Annals of Internal Medicine 445 (Sep. 1985).

Rowley, Clubb, Smith and Cabin, Right–Sided Infective Endocarditis as a Consequence of Flow–Directed Pulmonary–Artery Catheterization, 311:18 The New England J. Med. 1152 (Nov. 1, 1984).

J.M. Gore et al., *Handbook of Hemodynamic Monitoring,* 3 (1985).

Gore et al., A Community–Wide Assessment of the Use of Pulmonary Artery Catheters in Patients with Acute Myocardial Infarction, 92:4 Chest 712 Oct. 1987.

Baker et al., "Oesophageal Multipurpose Monitoring Probe", Anaesthia, 1983, vol. 38, pp. 892–897.

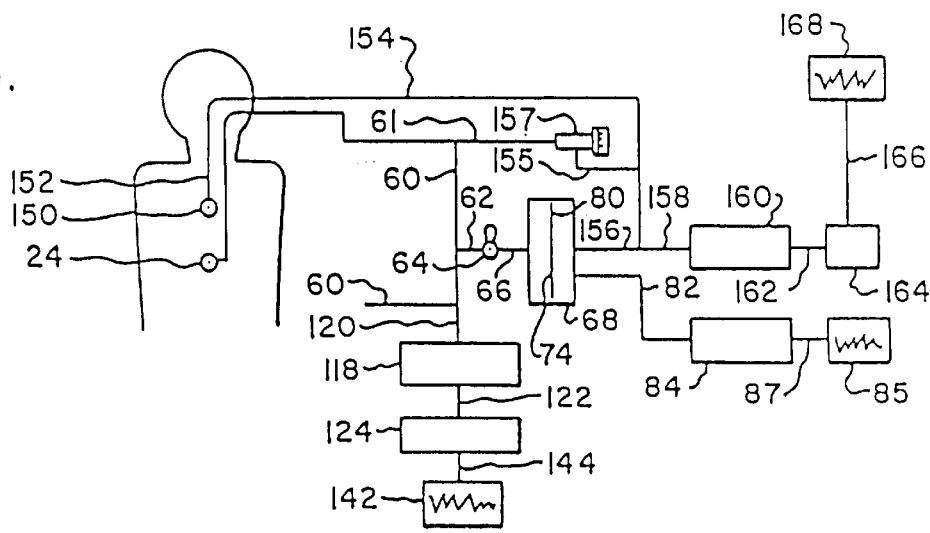
Fig. 13.
Fig. 1.
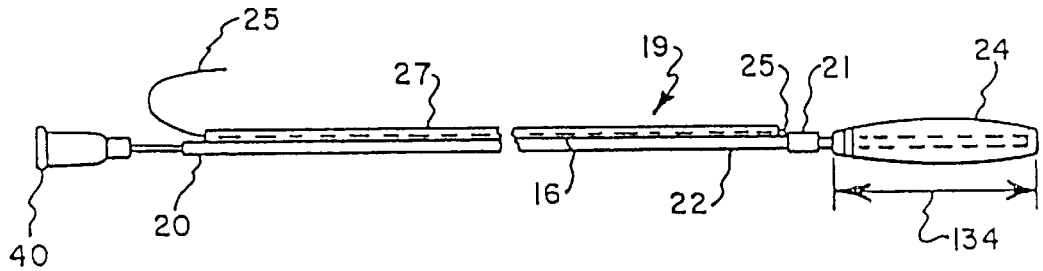
Fig. 2.
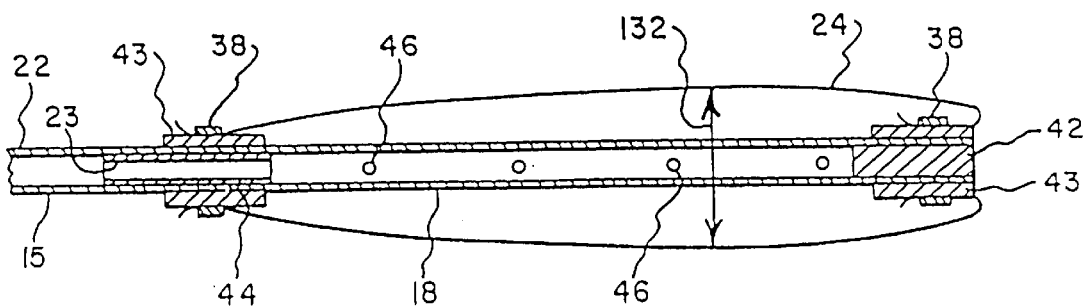

Fig. 4.
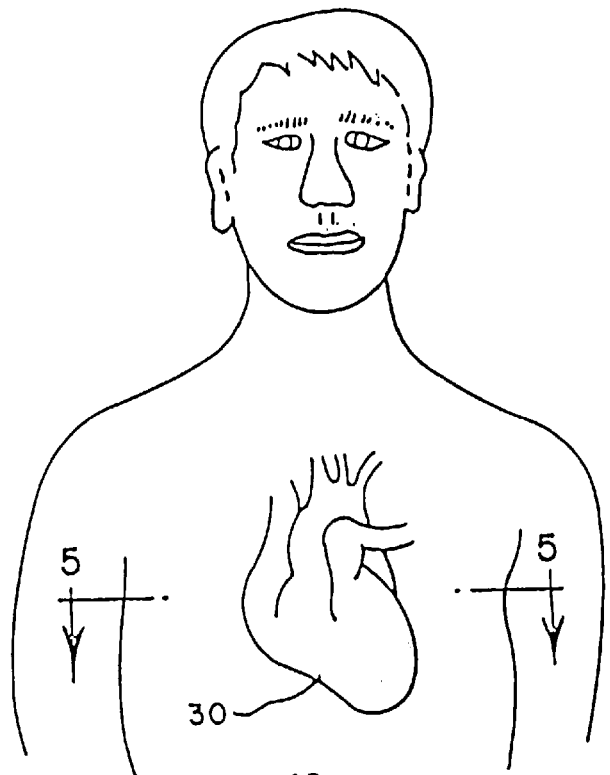
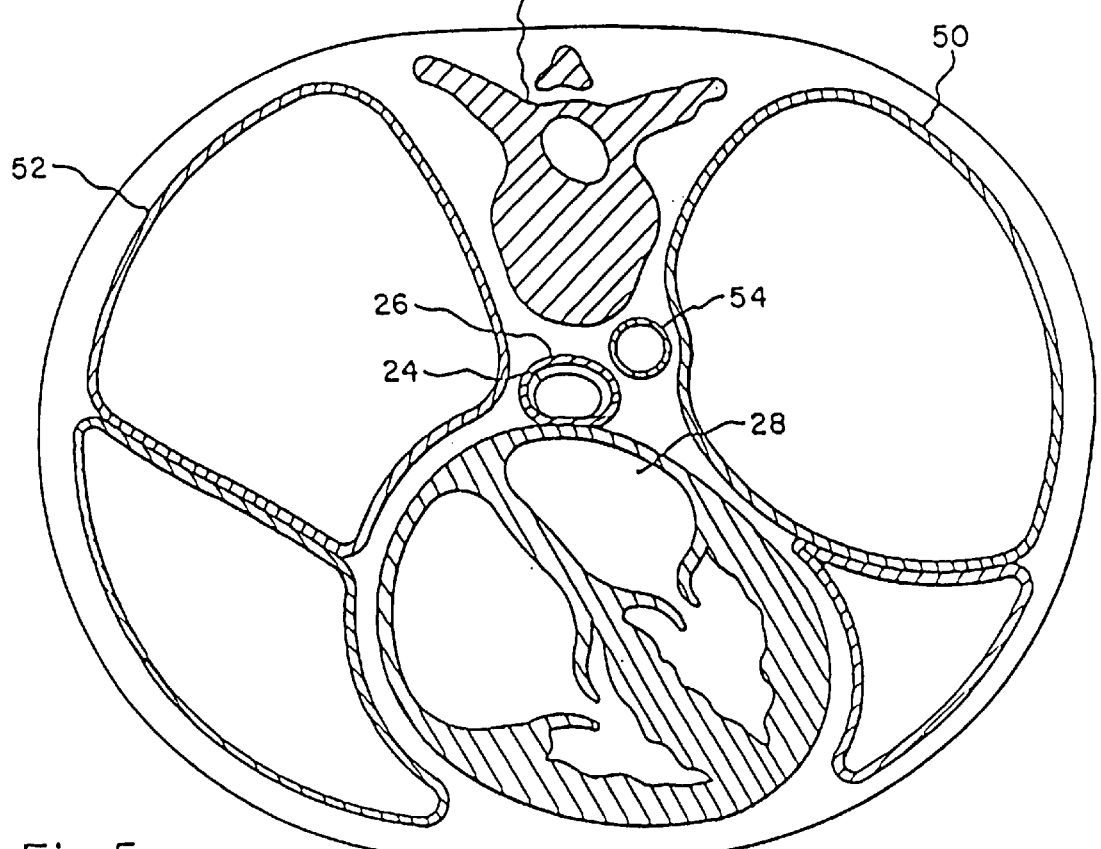
Fig. 5.

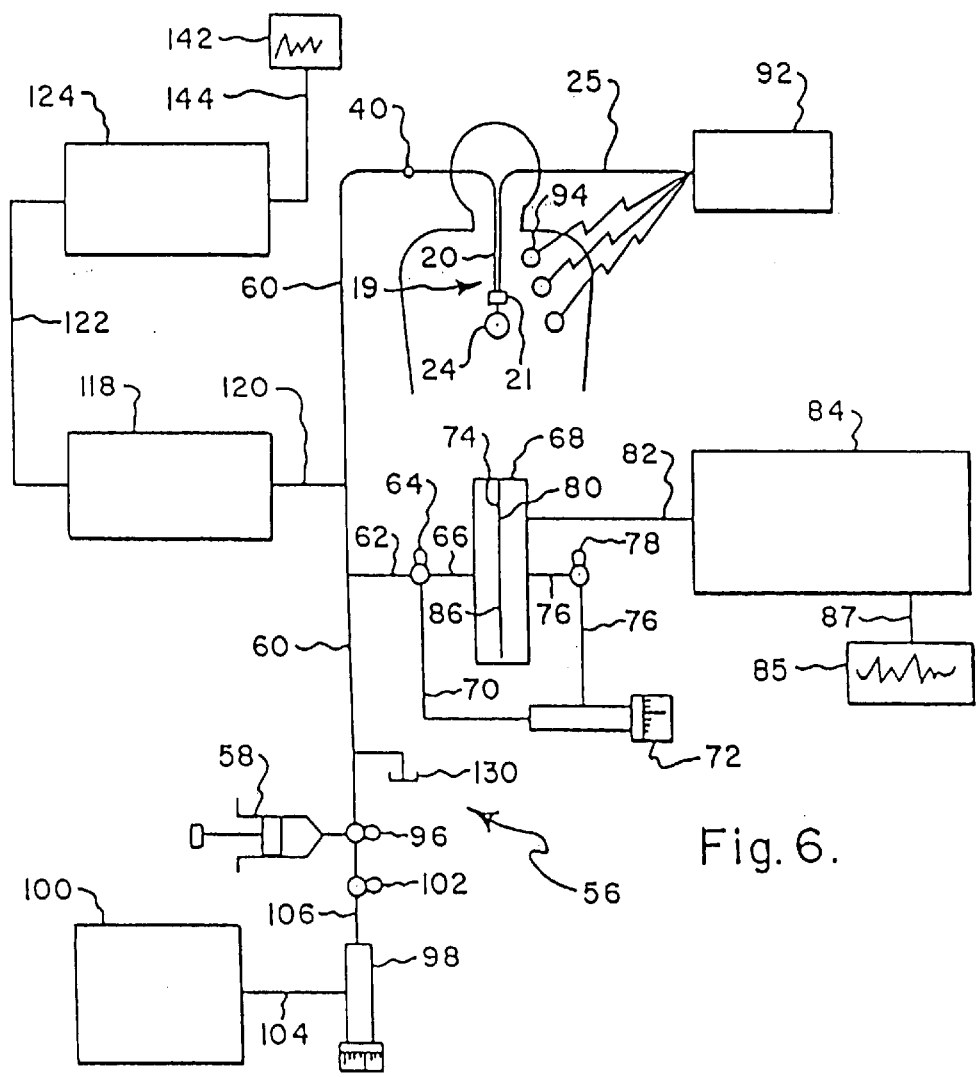
Fig. 6.
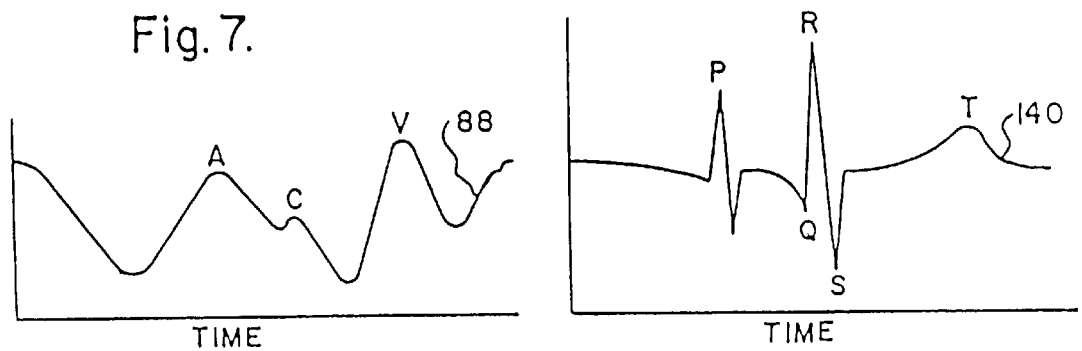
Fig. 7.
Fig. 8.

METHOD AND APPARATUS UTILIZING HEART SOUNDS FOR DETERMINING PRESSURES ASSOCIATED WITH THE LEFT ATRIUM

This is a division of application Ser. No. 08/377,466, filed Jan. 24, 1995 now U.S. Pat. No. 5,697,575, which is a continuation-in-part of co-pending U.S. patent application Ser. No. 08/114,775, filed Aug. 31, 1993, (now U.S. Pat. No. 5,398,692) which is a continuation of U.S. patent application Ser. No. 07/980,460, filed Nov. 23, 1992 (now U.S. Pat. No. 5,263,485), which is a continuation-in-part of U.S. Pat. No. application Ser. No. 07/717,854, filed Jun. 25, 1991 (now U.S. Pat. No. 5,181,517), which is a continuation-in-part of U.S. Pat. No. application Ser. No. 07/409,041, filed Sep. 18, 1989 (now U.S. Pat. No. 5,048,532). The disclosures thereof are hereby incorporated herein by reference.

TECHNICAL FIELD

The present invention relates generally to the quantitative determination of a pressure within a body with particular application to obtaining quantitative pressure values for determining mean left atrial pressure as well as mean left atrial transmural pressure and other pressures associated with the left atrium.

BACKGROUND ART

Ever since the English scientist Stephen Hales first measured the blood pressure by observing the blood rise in a tube inserted in an artery of a horse in 1733, scientists and physicians have sought better ways to measure blood pressure in people.

An instrument in common use for indirectly measuring blood pressure is a sphygmomanometer, which comprises an inflatable cuff which wraps around the upper arm above the elbow, a rubber bulb to inflate the cuff, and a device to measure the levels of pressure. It is well known that if the cuff is inflated to above systolic pressure, then slowly decompressed, oscillations corresponding to the heart rate will appear in the cuff pressure beginning somewhat above systolic pressure. These oscillations typically reach a maximum amplitude and then diminish until they are lost. The French physiologist, E. J. Marey, who discovered this phenomenon in 1876, reasoned that the peak amplitude of oscillation occurred close to mean arterial pressure. This hypothesis was confirmed by later investigators, and various methods of blood pressure determination based on the "oscillometric principle" were subsequently developed.

In 1905, Dr. N. S. Korotkoff proposed an auscultatory method of determining blood pressure. In this method, an arm cuff is inflated until it stops the circulation of blood beyond the cuff. Thereafter, a stethoscope is used to listen to the artery just distal to the cuff. Korotkoff hypothesized that the first sounds heard when the arm cuff is slowly deflated correspond to maximum pressure, whereas minimum pressure occurs when the sounds disappear. Later laboratory and clinical studies confirmed the accuracy of the auscultatory method, which eventually became universally adopted in clinical medicine.

The above techniques have heretofore been considered to provide insufficiently precise measurements for adequate management of cardiac pressures in critically ill patients. It has also not been possible to non-invasively determine left ventricular preload, which heretofore has been determined invasively by measuring the mean left atrial pressure or the pulmonary capillary wedge pressure.

In 1953, Lategola and Rahn demonstrated the efficacy of a flow-directed pulmonary artery catheter for the direct measurement of pulmonary artery pressure. Lategola and Rahn, A Self-Guiding Catheter for Cardiac and Pulmonary Arterial Catheterization and Occlusion, 84 Proc. Soc. Exp. Biol. Med. 667–668 (1953). In 1970, Swan, Ganz, and associates reported use of a flow-directed catheter in humans and further refined it for clinical use and for the direct measurement of pulmonary capillary wedge pressure. Swan, Ganz, Forrester, Marcus, Diamond, and Chonette, Catheterization of the Heart in Man With Use of a Flow-Directed Balloon-Tipped Catheter, 283:9 The New England J. Med. 447 (1970). At present, this catheter is an invaluable aid in the management of critically ill patients with pulmonary and cardiac disease, and the pulmonary wedge pressure (as an estimation of mean left atrial pressure or left ventricular filling pressure, commonly referred to as preload) is the standard of reference for intravascular volume management.

Numerous potential indications for pulmonary artery catheterization are now accepted. For example, catheterization is widely used in the evaluation and management of patients with acute myocardial infarction, for patients in shock, in the recognition of hypovolemia, in the treatment of patients suffering respiratory failure with persistent hypoxemia, and in patients with congestive heart failure. Catheterization is especially useful in assessing cardiac function in surgical patients, both pre-, intra-, and postoperatively. Since 1970, the ability to measure pulmonary capillary wedge pressure and cardiac output with the flow-directed catheter has resulted in the development of bedside hemodynamic monitoring, a procedure now performed daily in most hospitals in the United States. J. M. Gore et al., *Handbook of Hemodynamic Monitoring*, 3 (1985). Since the introduction of the Swan-Ganz catheter in 1970, it is reported that several million pulmonary catheters have been placed in patients with acute myocardial infarction. Gore et al., 92:4 *Chest*, 712 (October 1987).

Despite the widespread use of the pulmonary artery flow-directed catheter, the procedure is not without drawbacks. Complications that may arise from use of the catheter include pulmonary artery thrombosis or embolus, knotting of the catheter, rupture of the balloon and/or of a pulmonary artery, pulmonary hemorrhage, pneumothorax, hemothorax, right atrial thrombosis, sepsis, internal jugular stenosis or thrombosis, atrial and ventricular arrhythmias, electromechanical dissociation, right-sided endocardial lesions, and right-sided endocardial infection. Robin, The Cult of the Swan-Ganz Catheter, Overuse and Abuse of Pulmonary Flow Catheters, 103:3 Annals of Internal Medicine 445 (September 1985). In recent years, the safety and efficacy of pulmonary artery catheterization has become a subject of increased scrutiny and concern. One study suggests that flow-directed pulmonary artery catheterization may predispose patients to the development of right-sided endocarditis. Rowley, Clubb, Smith, and Cabin, Right-Sided Infective Endocarditis as a Consequence of Flow-Directed Pulmonary-Artery Catheterization, 311:18 The New England J. Med. 1152 (Nov. 1, 1984). The medical literature abounds with articles addressing the numerous medical complications associated with pulmonary artery catheterization. See, e.g., Murray, Complications of Invasive Monitoring, 15:2 Medical Instrumentation 85 at p. 89, March–April 1981, which lists various references related thereto. Perhaps the most serious allegation to date is that complications associated with the use of the pulmonary artery catheter in patients with acute myocardial infarction have resulted in an unusually and unacceptably high mortality rate. Robin, Death by Pulmonary Artery Flow-Directed Catheter. Time for a Moratorium? (editorial), 92:4 Chest 727 (October 1987).

In addition to the safety concerns, there is a relatively high monetary cost of critical care invasive monitoring, which cost may be minimized by the availability of a non-invasive procedure where indicated. Thus, a need has existed for a non-invasive and less costly improved method for accurately measuring blood pressure in the left atrium in people.

Invasive hemodynamic measurement nevertheless remains an important and feasible adjunct to clinical practice. Successful monitoring permits accurate determination of the state of the diseased heart and provides guidance for treatment and intervention to alter the course of a variety of diseases. It is recognized that modern Swan-Ganz catheters allow for the measurement of cardiac output, oxygen consumption, continuous mixed venous oxygen saturation, and cardiac pacemaking, and that many critically ill patients will require this degree of sophisticated monitoring. Nevertheless, given the knowledge of mean left atrial pressure and left atrial transmural pressure alone, there are numerous patients who could be safely managed in intermediate care units or on regular nursing floors. Certain patients undergoing general anesthesia could also benefit from less invasive monitoring of mean left atrial pressures. Furthermore, a less invasive technique for the measurement of mean left atrial pressure could be used to rationally screen patients to determine whether or not they would benefit from Swan-Ganz catheterization; otherwise, monitoring of mean left atrial pressure by such a less invasive technique may suffice to manage the patient outside the intensive care setting.

Thus, a long-felt need exists for a non-invasive method to accurately determine mean left atrial pressure. This is a ASK primary underlying objective of the present invention.

An esophageal catheter with a balloon having an inflated length and diameter of 3.1 cm. and positioned adjacent the left atrium has previously been used in an attempt to provide the shape of the curve of left atrial pressure. See Gordon et al, Left Atrial, "Pulmonary Capillary", and Esophageal Balloon Pressure Tracings in Mitral Valve Disease, British Heart J., 18: 327–340, 1956.

In order to record left atrial events, Gordon et al suggests, at page 330, that the esophageal balloon to be positioned adjacent the left atrium must be relatively small, "otherwise the tracings will be distorted by pressure or volume changes taking place at other than the desired left atrial level" and that it was "usually necessary to suspend respiration while the records were being made."

However, Gordon did not provide pressure measurement and, indeed, stated that his system was incapable of obtaining left atrial pressure values. Thus, Gordon et al states, at page 330, that "no attempt was made to measure absolute pressures from these tracings, as the amplitude of the pressure pulse is a function of the elasticity of the system, the amount of fluid in the balloon and the initial pressure within it, as well as the intra-atrial pressure." As again indicated at page 338 of Gordon et al, one of the drawbacks of the Gordon et al system is the inability to obtain absolute left atrial pressure values. That was more than 30 years ago.

A concern when attempting to pick up left atrial pressure waves using balloon-tipped esophageal catheters is the problem of insuring that the balloon is properly positioned behind the left atrium. In connection with the placing of electrodes for transesophageal heart pacing, it has been suggested that a positioning balloon may be inserted on the distal end of an esophageal catheter to anchor the catheter in the stomach. Since the distance between the left atrium and the stomach (gastroesophageal junction) is relatively constant in an adult, the pacing electrodes could then be affixed to the catheter at this distance proximal to the stomach balloon. See Andersen et al, Trans-Esophaaeal Pacing, PACE, Vol. 4, July–August, 1983, pp. 674–679. However, this process is not suitable for use with non-adults since the gastroesophageal junction to left atrial distance will not be constant but will vary for neonates and children. It has also been suggested, in connection with observing the esophageal pulse in mitral valve disease, that an electrode may be used to position an esophageal balloon behind the left atrium by attaching it to the catheter just above the balloon to measure the esophageal electrocardiogram from behind the left atrium. See Zoob, The Oesophageal Pulse in Mitral Valve Disease, British Heart J., Vol. 16, 1954, pp. 39–48. Also see Brown, A Study of the Esophageal Lead in Clinical Electrocardiography, American Heart J., Vol. 12, No. 1, July, 1936, pp. 1–45; and Oblath and Karpman, The Normal Esophageal Lead Electrocardiogram, American Heart J., Vol. 41, 1951, pp. 369–381.

While mean left atrial pressure is considered important, pulmonary venous transmural pressure or mean left atrial transmural pressure (hereinafter called "transmural pressure") is considered to be a more clinically useful physiologic value because it allows physicians to more precisely determine when a patient could go into pulmonary edema from heart failure or volume overload, and it also allows an assessment of the effect of positive end expiratory pressure with ventilated patients. For the purposes of this specification and the claims, transmural pressure is equal to the difference between mean left atrial pressure and the intrapleural pressure. The tissue pressure in the chest (mediastinum) reflects the intrapleural pressure, which is usually sub-atmospheric at end expiration during regular breathing while sitting erect. However, the transmural pressure has not been commonly used by physicians because it has heretofore not been readily obtainable and available.

It is an object of the present invention to non-invasively obtain quantitative pressure measurements to readily determine a person's mean left atrial pressure as well as the transmural pressure safely, accurately, and reliably. As used herein and in the claims, the terms "transmural pressure" and "pulmonary venous transmural pressure" are meant to refer to the mean left atrial transmural pressure.

It is another object of the present invention to obtain such measurements economically and easily.

It is a further object of the present invention to provide a method for determining a person's mean left atrial and transmural pressures which may be administered by a non-physician.

It is still another object of the present invention to non-invasively obtain quantitative pressure measurements to readily determine other pressures associated with the left atrium safely, accurately, and reliably.

SUMMARY OF THE INVENTION

In order to non-invasively and readily determine a person's mean left atrial and transmural pressures safely, accurately, and reliably, in accordance with the present invention a balloon is inserted into the person's esophagus and positioned adjacent the left atrium and inflated, and the mean balloon pressure is measured when the intensity of heart sounds, after they are transmitted through the balloon, is at a peak. This peak sound intensity is indicative of unloading of the balloon (or balloon fabric) due to the mean balloon pressure being equal to the mean pressure adjacent the balloon, i.e., a pressure effected by the person's mean left atrial pressure. This pressure, after adjustment, as discussed below, for the effects of the weight of the heart and of intrapleural pressure, can be used to determine an approximately the mean left atrial and transmural pressures.

The effects of heart weight and intrapleural pressure may be determined by moving the balloon to or positioning another balloon at a position in the esophagus away from where the heart presses on the esophagus and, while filling the balloon, noting the pressure at an initial slope change (which represents approximately the intrapleural pressure). The pressure contribution of heart weight may be calculated to be a pressure at an initial slope change as the balloon fills while behind the heart less the pressure at an initial slope change as the balloon fills while away from the heart. This pressure contribution is subtracted from the mean balloon pressure at the peak sound intensity to obtain a more precise determination of mean left atrial pressure.

Transmural pressure, which is equal to the mean left atrial pressure less the intrapleural pressure, is as a result equal to the mean balloon pressure at the peak sound intensity less the pressure at the initial slope change. Thus, a determination of transmural pressure advantageously does not require the movement of the balloon (or other balloon) to a different location in the esophagus.

The above and other objects, features, and advantages of the present invention will be apparent in the following Best Mode for Carrying Out the Invention when read in conjunction with the accompanying drawings in which like reference numerals denote the same or similar parts throughout the several views.

BRIEF DESCRIPTION OF THE DRAWINGS

FIG. 1 is a side view of a combination of a balloon-containing catheter and an electrode-containing catheter in accordance with the present invention with the balloon inflated.

FIG. 2 is an enlarged side sectional view of the balloon of FIG. 1.

FIG. 4 is a front sectional view of the human body illustrating the position of the heart.

FIG. 5 is a top sectional view of the human body, taken along lines 5—5 of FIG. 4, at the level of the seventh thoracic vertebra and with the balloon of FIG. 1 in the esophagus.

FIG. 6 is a schematic view of apparatus, including the balloon-containing catheter of FIG. 1, which embodies the present invention.

FIG. 7 is a pressure trace of the left atrial pressure during one cardiac cycle as sensed by the balloon of FIG. 1 when adjacent the left atrium.

FIG. 8 is a graph of an esophageal electrocardiogram of the left atrium during one cardiac cycle.

FIG. 13 is a schematic view of an alternative embodiment of the present invention, it being understood that this embodiment is meant to include the portion of apparatus of FIG. 6 which is connected to line 60.

BEST MODE FOR CARRYING OUT THE INVENTION

Figure 3:
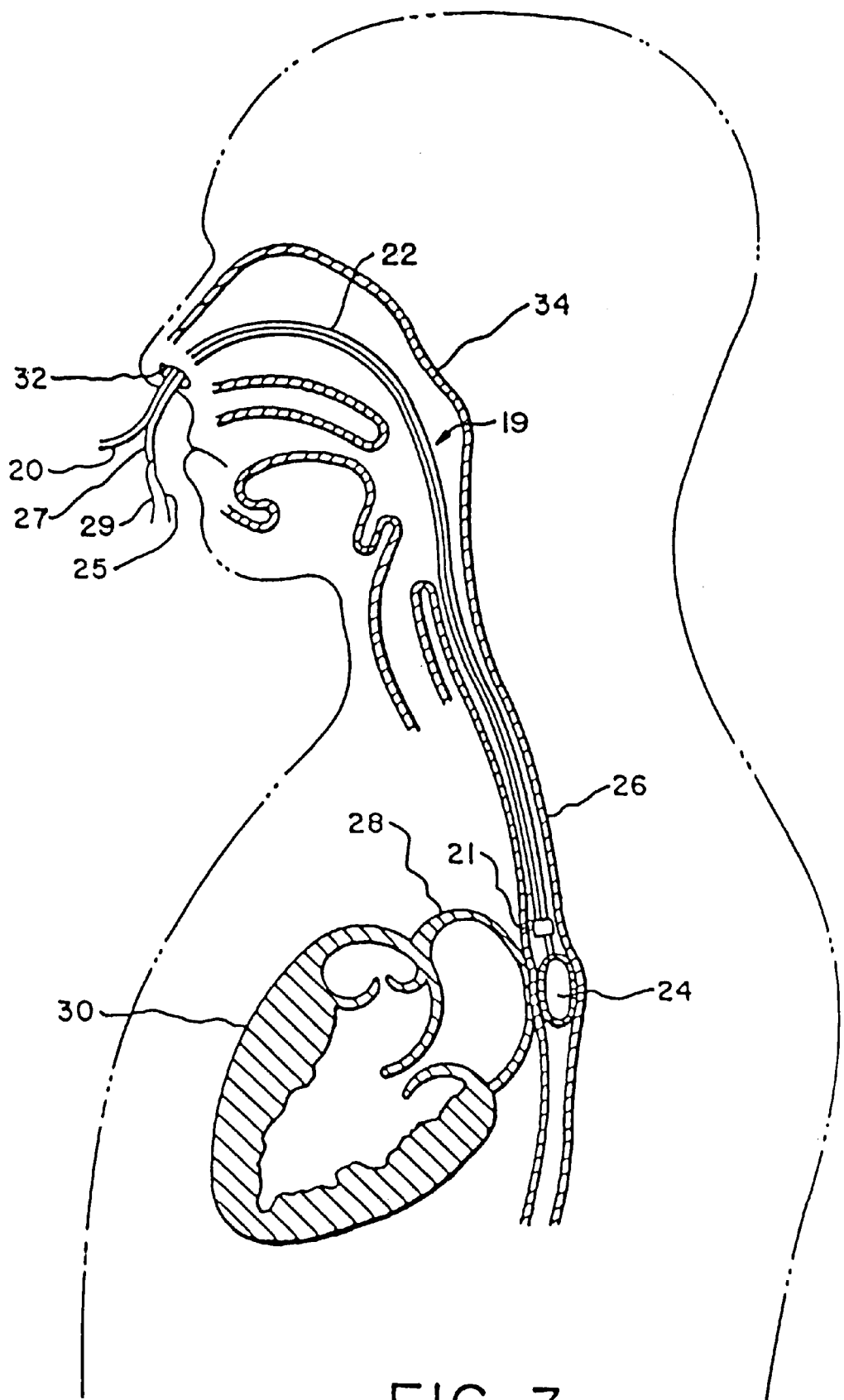
FIG. 3 is a partial left lateral sectional view of the human body taken along the mid-sagittal plane and showing the balloon of FIG. 1 within the esophagus and adjacent the left atrium of the heart.

The use of the oscillometric principle to determine mean left atrial pressure or a pressure associated therewith by measuring mean pressure in an esophageal balloon gradually being inflated adjacent to the left atrium when the amplitude of balloon pressure oscillations effected by the left atrial pressure is at a peak is discussed in the aforesaid U.S. Pat. No. 5,263,485 and is discussed herein with reference to FIGS. 1 to 13. The use of the oscillometric principle in accordance with the present invention to determine mean left atrial pressure or a pressure associated therewith by measuring mean pressure in the balloon when the intensity of a sound wave, after it is transmitted through the balloon, is at a peak is discussed thereafter with reference to FIGS. 14 to 18. As applicable, the principles discussed with reference to FIGS. 1 to 13 will apply to the present invention as discussed with reference to FIGS. 14 to 18.

Referring to FIGS. 1 and 2, there is illustrated generally at 19 catheter apparatus including a hollow catheter 20 comprising a length of flexible tubing 22 having a bore or lumen 23 and on one end of which is attached a balloon 24 for flow communication with the lumen 23 for pressurization of the balloon and for sensing the pressure thereof. An electrode 21 may be positioned just above the balloon 24 for obtaining an esophageal electrocardiogram and an electrical lead 25, within a second catheter 27, provided thereto, as will be discussed in greater detail hereinafter.

Referring to FIG. 3, there is illustrated the placement of the balloon 24 within the esophagus 26 of a human body for the purpose of sensing the pressure of the left atrium 28 of the heart 30. The catheter 20 is inserted balloon first through nasal passage 32, pharynx 34, then into the esophagus 26. If desired, the balloon may alternatively be inserted through the mouth. As shown in FIG. 3, the outer wall of the left atrium 28 is adjacent and essentially in direct contact with the outer wall of the esophagus 26, and advantage is taken of this relationship to determine mean left atrial pressure, transmural pressure, and associated pressures by means of the balloon 24 thusly inserted non-invasively into the esophagus 26 and positioned therealong adjacent the left atrium so as to be sufficiently affected thereby to sense left atrial pressure, as will be discussed in greater detail hereinafter.

The tubing 22, which may have an inner diameter of perhaps approximately 0.050 inch, and balloon may be composed of any suitable flexible, chemically inert, non-toxic material such as polyvinyl chloride for withstanding operating pressures without significant expansion. A preferred tubing is composed of an 83 to 85 durometer polyvinyl chloride sold by Colorite Plastics Co. of Richfield, N.J. and identified as its Unichem polyvinyl chloride no. 8311 G-015. A preferred balloon material is a 70 durometer polyvinyl chloride from the same source and identified as its Unichem polyvinyl chloride no. 7011 G-015. Alternatively, the tubing and balloon may be composed of a 90 durometer polyurethane such as sold by Miles Incorporated of Pittsburg, Pa. as Texin 990A polyurethane or sold by B. F. Goodrich of Cleveland, Ohio as Fstane 5810 polyurethane. Another suitable tubing is a Tygon® brand polyvinyl chloride tubing having an inner diameter of approximately 0.050" which is a product of Cole-Parmer Instrument Co., 7425 North Oak Park Avenue, Chicago, Ill. 60648-9930, as shown on page 636 of the Cole-Parmer 1989–90 Catalog. The tubing 22 has a suitable length which may be perhaps 80 cm. The tubing 22 may desirably have markings (not shown) along the length thereof to indicate distance therealong so that the balloon 24 may be initially positioned approximately adjacent the left atrium 28. The tubing may contain a portion 18 which extends over the length of the balloon 24 and a portion 15 which extends from the balloon. Portions 15 and 18 are connected by means of a stainless steel ferrule 44 over which the tubing is press fit. The distal end of the balloon is closing by plugging by a cylindrical plug 42 of stainless steel or the like over which tubing portion 18 is press fit. At each balloon end, a sleeve 43 is fitted over the tubing portion 18 to provide a larger diameter for securing the balloon fabric. Each balloon end is then sealed by surgical thread 38 and/or silicone cement. A plurality of apertures 46 are provided in the tubing (portion 18) wall over a distance from the closed end 42 equal to less than the balloon length to provide flow communication between the tubing 22 and the interior of the balloon 24 for inflating the balloon and for sensing pressure therein. The balloon 24 fits over the tubing portion 18 containing the apertures 46 and is attached to the tubing 22 at end portion 42 and at ferrule or second portion 44 between which portions are the apertures 46, as illustrated in FIG. 2. Pressurization and sensing lines may be attached at the end 40, which is opposite the balloon end 42, as will be discussed in greater detail hereinafter.

However, other suitable means may be used for such attachment. For example, the balloon may be fixed over the end of a catheter the end of which is plugged. The balloon 24 may be constructed of any suitable flexible non-toxic film which can withstand operating pressures without rupture or irreversible deformation. The balloon 24 may have a capacity of perhaps about 2 milliliters. When inflated within the pressure range for determining mean left atrial pressure, the balloon 24 takes on a generally cylindrical shape, as illustrated in FIGS. 1 and 2. The thickness of the material of which the balloon 24 is made is perhaps about 0.0005". The balloon 24 should function properly in any rotational orientation around the longitudinal catheter axis. The balloon 24 may, for example, be constructed of low density polyethylene film such as Extrel® SF brand polyethylene film, a product of Exxon Chemical Co., Polymers Group, Division of Exxon Corp., 351 North Oakwood Road, Lake Zurich, Ill. 60047-1562.

Alternatively, a catheter in accordance with the present invention may be extruded with the balloon suitably fitted thereon such as by heat sealing or RF (radio frequency) welding for either polyvinyl chloride or polyurethane materials. If the balloon and tubing are composed of polyvinyl chloride, UV (ultraviolet) welding is preferably employed. A 40 percent barium sulfate stripe may be put in the resin for the tubing to make it radiation-opaque so that it may be picked up on x-rays.

Referring to FIGS. 4 and 5, it should be noted that the esophagus 26 is sandwiched between the left atrium 28 and the vertebral column 48 so that when the balloon 24 is positioned adjacent the left atrium 28 the vertebral column 48 acts similarly as an anvil for effective action of the left atrium pressure on the balloon 24 to affect the pressure therein as will be described hereinafter. The esophagus 26 is flanked by the left and right lungs 50 and 52 respectively. The aorta 54 is positioned generally between the esophagus 26 and the left lung 50 and in proximity to the vertebral column 48, as shown in FIG. 5.

Referring to FIG. 6, there is illustrated generally at 56 apparatus for pressurizing the balloon 24 and for sensing the pressure therein. For the purpose of precisely positioning the balloon 24 adjacent the left atrium 28, the balloon 24 is first statically filled with a predetermined quantity of perhaps 1.4 milliliter of air via syringe 58, with stop cock or valve 96 suitably open for passage of the air therefrom through line 60 to tubing 22, to which line 60 is suitably attached at the end portion 40.

The balloon pressure is transmitted from line 60 through line 62 to four-way stop cock or valve 64 which transmits the pressure through line 66 to one side 74 of the diaphragm 86 of a differential pressure transducer 68 and through line 70 to filter 72. Transducer 68 may, for example, be a Validyne model DP7 differential pressure transducer provided by Validyne Engineering Corp., 8626 Wilbur Avenue, Northridge, Calif. 91324. Pressure from the filter 72 is transmitted through line 76 and stop cock or valve 78 to the other side 80 of the transducer 68. The transducer 68 converts the net pressure signal acting on the diaphragm 86 to an electrical signal which is transmitted through line 82 to a first signal processor 84. Processor 84 may be any suitable conventional electronic signal processing circuit which amplifies and otherwise processes and conditions the electrical signal representations of pressure and communicates these signals to a display means 85 via line 87. Display means 85 may be a digital display, a strip chart recorder, a cathode ray tube, or any other suitable device for displaying or utilizing the signals from processor 84.

The balloon 24 will not only sense atrial pressure but will also record normal peristaltic waves from swallowing as well as pressure excursions from normal breathing. Peristaltic waves are easily distinguished by their high amplitude (up to 100 cm of water) and relative infrequency and can therefore be ignored. Respiratory excursions (typically from −10 to +10 cm of water at frequencies of 0.1 to 0.8 Hertz) can interfere with left atrial pressure wave form and measurement. They are therefore filtered out during signal processing as described hereinafter.

Filter 72 is a low pass mechanical filter such as, for example, a Nupro® micrometer needle valve connected as shown in FIG. 6, a product of Nupro Company of 4800 East 345th Street, Willoughby, Ohio 44094. The unprocessed signal carrying both the higher frequency cardiac wave form (generally 1.5 to 9.0 Hertz) effected by left atrial pressure and the lower frequency respiratory wave form (generally 0.1 to 0.8 Hertz) goes directly to the first side 74 of the differential pressure transducer 68 via line 66. An identical signal is also transmitted to the variable control valve 72. By restricting an orifice (not shown) in filter 72, in accordance with principles commonly known to those of ordinary skill in the art to which this invention pertains, the balloon pressure wave is filtered to selectively pass the lower frequency component, which includes respiratory artifact, through line 76 and valve 78 to the other side 80 of the differential transducer 68, and the higher frequency component is excluded. This in effect allows the respiratory artifact arriving almost in phase on both sides of the transducer diaphragm 86 to cancel itself out so that the cardiac wave form is recovered and outputted as an electrical signal through line 82 to the first signal processor 84.

With the balloon inflated, it is precisely positioned adjacent the left atrium 28 by moving it up or down the esophagus 26 by withdrawing or inserting the catheter 20 at the nose until a typical left atrial pressure wave form, illustrated at 88 in FIG. 7, is seen on the pressure trace from the first signal processor 84. As previously discussed, this wave form 88 comprises the balloon pressure signal with the lower frequency respiratory wave form filtered out. This wave form 88 may be confirmed as being a typical left atrial pressure wave form by comparison with a simultaneous esophageal electrocardiogram, illustrated at 140 in FIG. 8, which is recorded by a conventional electrocardiograph, illustrated at 92 in FIG. 6. Electrocardiogram 140 is obtained by the use of a stainless steel electrode, illustrated at 21, which is suitably attached to the catheter 20 just above the balloon 24. However, the electrode 21 may be otherwise adjacent the balloon 24. For example, an electrode for this purpose could comprise conductive material on the surface of the balloon. An electrical lead 25 is attached to the electrode and extends within a second catheter 27 and to electrocardiograph 92 for transmitting the signals picked up by the electrode 21 for processing therein. The lead 25 may, for example, be silvered 30 AWG wire-wrapping wire provided by OK Industries, 4 Executive Plaza, Yonkers, N.Y. 10701. The catheters 20 and 27 may be held together by suitable securing means such as, for example, cyclohexanone glue 16. Alternatively, a double-lumen catheter of pre-formed polyvinyl chloride may be used. The electrode 21 is preferably in the shape of a ring which encircles catheter tubing 22 so as to insure that it will be suitably positioned without interference by tubing 22 for sensing left atrial electrical activity. In accordance with conventional practice, it may be required that skin electrodes 94 also be hooked-up to the subject. The wave form 140 is characterized by a wave portion (which heralds atrial depolarization) which reaches a high voltage and becomes bi-phasic with a sharp upstroke and shows an intrinsicoid deflection. Thus, points A, C, and V, shown on wave form 88 in FIG. 7, are three essential components of the left atrial pressure wave, and these points are known to correspond to points P, R, and T respectively on the electrocardiogram 140 of FIG. 8 thus confirming that the wave form 88 is a typical left atrial pressure wave form.

When, as the balloon and esophageal electrode are moved up and down the esophagus, a typical left atrial wave form, similar to wave form 88, is sensed on the pressure trace from the first signal processor 84, which indicates that the balloon 24 is suitably positioned adjacent the left atrium 28, the balloon 24 is then fixed in place by applying tape over the catheter 20 and onto the upper lip just beneath the nose. The distinctiveness of this wave form, confirmed by use of electrode 21, may desirably reduce the level of skill required for proper positioning of the balloon. Alternatively, a conventional surface or skin electrocardiogram may be obtained, by use of electrodes 94 on the subject's body and wired to electrocardiograph 92, for comparison with wave form 88 to determine when the balloon is correctly positioned. However, the use of the esophageal electrocardiogram 140 for this purpose is considered preferable since it may provide a more distinctive wave form which is more easily recognized. The use of either the esophageal or skin electrodes for positioning the balloon is advantageously suitable for use with the wide range of body size from premature neonates to adult men.

Other means for suitably positioning the sensing balloon may alternatively be used. For example, as illustrated in the aforesaid U.S. Pat. No. 5,263,485, a positioning balloon may be positioned on a catheter to contact the esophago-gastric junction at the stomach of an adult and a sensing. balloon positioned on a separate catheter and at a distance from the positioning balloon which approximates the relatively constant distance in an adult between the esophago-gastric junction and the left atrium. This distance is of course relatively constant in adults but not in premature neonates and infants. For another example, the sensing balloon may be positioned by use of an esophageal electrocardiogram alone, as discussed in "Optimal Mode of Transesophageal Atrial Pacing" by M. Nishimura et al, *American J. of Cardiology*, vol. 57, 1986, p. 791–796. In regard to pacing, this article states that "the point showing the largest unipolar atrial electrogram was thus considered the optimal site of pacing for both bi-polar and uni-polar stimulation." The left atrium may be assumed to be 1 to 2 cm. distal to this point. Also see "Trans-esophageal Atrial Pacing Threshold: Role of Interelectrode Spacing, Pulse Width and Catheter Insertion Depth" by D. Benson et al, *American J. of Cardiology*, 1984, p. 63–67.

As previously discussed, the pressure wave form 88 is insufficient for determining mean left atrial pressure due to its amplitude being a function of the elasticity of the system, the amount of gas in the balloon, and the initial pressure within it, as well as the intra-atrial pressure and the surrounding tissue pressure. With the balloon 24 precisely positioned, processing can begin for accurately and noninvasively determining the mean left atrial and transmural pressures or other pressures associated with the left atrium, as discussed hereinafter.

After proper placement has been accomplished, sensing balloon 24 is initially evacuated to perhaps −10 to −12 cm of water pressure, less than the minimum expected pressure to be measured using syringe 58, with the stop cock 96 open thereto. This purges the system of any gas, prior to beginning a measurement, to insure consistency, accuracy, and reliability of pressure measurements. The system is similarly also purged of any residual gases between measurements.

After the balloon 24 has been properly placed adjacent the left atrium 28 and evacuated, it is gradually inflated with air or another suitable inert gas such as, for example, nitrogen gas or a suitable liquid such as, for example, water for the purpose of determining mean left atrial pressure as hereinafter described. The use of a liquid may provide enhanced gain. If a liquid is used, it may be provided to line 60 by means of a liquid-filled syringe to which is attached a suitable mechanical or hydraulic pressurization device. The use of air may simplify the equipment and its use and may therefore be preferred for this purpose. A source of air under a sufficient pressure such as, for example, 40 psig for inflating the balloon 24 is illustrated at 100. With stop cocks or valves 96 and 102 opened to connect the metering gas supply valve 98 with the line 60 and with syringe 58 closed to line 60 by valve 96, the gas from source 100 is routed through line 104 to the metering valve 98 where it is released to line 106 and through stop cocks 102 and 96 and line 60 to catheter 20 in metered quantity for gradually inflating the balloon 24. As used herein and in the claims, the term "line", unless otherwise specified, is meant to refer to tubing, a catheter, an electrically conductive wire, or other suitable means for transmitting a pressure or electrical signal. Valve 98 is a Nupro® brand micrometer needle valve, a product of Nupro Company of 4800 East 345th Street, Willoughby, Ohio 44094, which is constructed to allow a broad range of near constant flow rates against back pressures to a maximum of about 50 cm water (0.74 psi). It is precalibrated to provide gas flows up to about 4 milliliters per minute on average. Other suitable valves may alternatively be provided. Metering valve 98 is thus opened to provide a suitable gas flow such as a flow of approximately 1.0 milliliter per minute for gradually filling the sensing balloon 24 at a constant rate.

Alternatively, the balloon may be filled by a syringe that is controlled by a stepping motor and that employs a restricted orifice between the syringe and line 60 so as to isolate the syringe from the line with a mechanical low-pass filter.

While not wishing to be bound by theory here or elsewhere in this specification, the following is believed to occur as the sensing balloon 24 is pressurized. The gradual filling of the sensing balloon 24 causes the pressure therein to increase at a generally slow steady rate which, in accordance with the theory of the previously discussed oscillometric effect, is affected by the atrial pressure causing oscillations therein as well as by respiratory waves. As the mean balloon pressure approaches the mean left atrial pressure, the atrial pressure oscillations of balloon pressure increase in intensity or amplitude until the balloon pressure resonates maximally, i.e. reaches a peak amplitude, when the mean balloon pressure approximates the mean left atrial pressure. Thereafter, as the mean balloon pressure continues to increase, the amplitude of oscillations due to the atrial pressure decreases. More specifically, the balloon pressure oscillates maximally when its expansion has increased the pressure in the tissue surrounding the left atrium to the point where the mean tissue pressure equals mean left atrial pressure (MLAP). Thus, it may be said that the balloon works best as a pressure transmitter when it is unloaded, i.e., when the mean pressure on both sides of the balloon wall are equal, resulting in the greatest amplitude of balloon pressure oscillations when the mean balloon pressure equals mean left atrial pressure.

Figure 12:
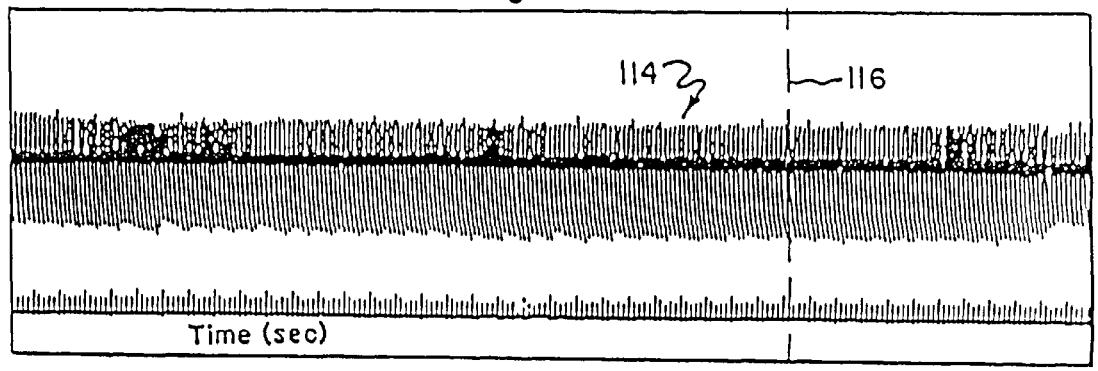
FIG. 12 is a graph of an electrocardiogram taken simultaneously with the pressure traces of FIGS. 9, 10 and 11.

FIGS. 9 to 12 are illustrations of four electronic displays or tracings used to record and display the absolute balloon pressure wave form 108 (FIG. 9), the mean balloon pressure wave form 110 (FIG. 10), the differential signal 112 with added gain from the signal processor 84 (FIG. 11), and a simultaneous electrocardiogram 114 (FIG. 12). Vertical line 116 in each of FIGS. 9 to 12 represents the same point in time. A comparison of the electrocardiograms 140 and 114 in FIGS. 8 and 12 respectively indicates that the time scale for FIGS. 7 and 8 is greatly expanded relative to the time scale for FIGS. 9 to 12, i.e., the wave form 140 in FIG. 8 covers a period of about a second, and a multitude of such waves over a multitude of seconds is shown in FIG. 12.

The absolute balloon pressure wave form 108 is obtained from a suitable transducer 118 connected to line 60 via line 120. The transducer 118 may, for example, be a Cobe CDX III transducer provided by Cobe Laboratories, Inc., 1185 Oak Street, Lakewood, Colo. 80215. The transducer 118 converts the balloon pressure signal in line 120 to an electrical signal which is transmitted through line 122 to second signal processor 124, which is a suitable conventional electronic signal processing circuit which suitably processes and conditions the electrical signal representations of pressure and transmits these signals to a suitable display means 142, which may be similar to display means 85, via line 144. The processor 124 amplifies the signal for display as shown by tracing 108 in FIG. 9. Signal processor 124 also suitably processes the signal, in accordance with principles commonly known to those of ordinary skill in the art to which this invention pertains, to provide an electronic mean thereof as shown by tracing 110 in FIG. 10. The transducer 118 is referenced to one atmosphere of pressure absolute.

It should be recognized that other suitable analog or digital electronic signal processing means can be employed to filter, amplify, compare, and otherwise process the signals. Both pressure transducers 68 and 118 are suitably calibrated against a water manometer prior to use.

A suitable relief valve 130 is provided in line 60 to protect the system 56 and the patient from over-pressurization. The relief valve 130 is set to open at a suitable pressure of perhaps 50 mm of mercury pressure to vent the tubing and balloon to atmosphere in order to prevent dangerously high pressure such as might cause the balloon to rupture.

The absolute balloon pressure wave form 108 is comprised of low amplitude high frequency oscillations effected by left atrial pressure which are superimposed on high amplitude low frequency respiratory oscillations which are in turn super-imposed on the gradual increase in balloon pressure provided by gas supply valve 98. The mean balloon pressure wave form is shown at 110 in FIG. 10. By "mean balloon pressure" is meant, for the purposes of this specification and the claims, the balloon pressure at the mean of each of the high frequency (greater than about 0.8 Hertz) oscillations. Stated another way, the "mean balloon pressure" wave form 110 is the absolute balloon pressure wave form 108 with the high frequency oscillations removed therefrom. When a signal is filtered, waves which are removed therefrom do not appear in the output while those which are passed or extracted do appear in the output. The abrupt slope change indicated at 200 from a fast to a slowed rate of pressure increase is indicative of the equalization of balloon pressure with the surrounding tissue pressure prior to balloon expansion.

The differential signal 112 is provided by the signal processor 84 after low frequency oscillations representing the respiratory artifact are filtered out by the differential pressure transducer 68 so that the left atrial pressure wave form is recovered. In addition, the rising absolute pressure due to the gradual inflation of the balloon 24 (which is treated by the filter 72 similarly as a low frequency oscillation and thus passed to transducer side 80) is also cancelled out by the differential transducer 68 so that the pressure signal 112 processed by signal processor 84 is on a steady base line. The signal 112 is then further filtered electronically, amplified, and displayed by the signal processor 84 on display 85.

Wave form 112 may alternatively be obtained by electronically inverting the mean balloon pressure wave form 110 and adding the inverted wave form to the absolute balloon pressure wave form 108 and amplifying the oscillations obtained.

The use of a bias balloon 150 for alternatively eliminating respiratory artifact to obtain signal 112 is illustrated in FIG. 13. The pressure in balloon 24 is transmitted through lines 60, 62, and 66 to one side 74 of differential pressure transducer 68 similarly as illustrated in FIG. 6. This pressure, which is also transmitted through line 120 to transducer 118 and converted to an electrical signal which is processed and displayed on display 142, includes the effects of respiratory artifact as well as atrial pressure. The bias balloon 150, similar to balloon 24 and similarly inserted by means of a catheter 152, which may be similar to or a part of catheter 20, may also be pressurized via line 60 as hereinafter discussed. Bias balloon 150 is inserted into the esophagus intermediate the position of the left atrium and the nasal or mouth passage, i.e., perhaps 10 or 11 cm. or more above the position of balloon 24, so that the pressure therein is not affected by left atrial pressure. But bias balloon 150 does sense respiratory artifact, i.e., pressure swings generated by respiration, and therefore may be said to reflect esophageal pressure and thus record the respiration induced fluctuation in esophageal pressure. The bias balloon pressure is transmitted through lines 154 and 156 to the other side 80 of differential pressure transducer 68. Thus, a pressure effected by absolute left atrial pressure plus respiratory artifact is applied to one side 74 of transducer 68, and a pressure effected by respiratory artifact is applied to the other side 80. The difference, representative of left atrial pressure without the respiratory artifact, is outputted as an electrical signal through line 82 to signal processor 84 which transmits a suitably processed signal of the resulting difference wave through line 87 to signal display 85, which may be similar to display 142. One advantage of bias balloon 150 is that its use will eliminate respiratory artifacts regardless of their frequency. If desired, the bias balloon 150 could also be used to independently measure simultaneous esophageal pressure by transmitting the bias balloon pressure from line 154 via line 158 to transducer 160, which may be similar to transducer 118, which converts the pressure to an electrical signal which is then transmitted via line 162 to signal processor 164, which may be similar to processor 124, in which the signal is suitably processed and transmitted via line 166 to display 168, which may be similar to display 142.

The aforesaid U.S. Pat. No. 5,263,485 describes a multi-lumen catheter providing a first passage for flow communication with a balloon similar to balloon 24 for determining mean left atrial pressure, a second passage for serving as a naso-gastric tube, and a third passage which serves as a transmission passage for an esophageal stethoscope and which incorporates a temperature sensor. Transmission of heart sounds via the third passage is facilitated by a plurality of apertures in the catheter tubing for the third passage, and these apertures are covered by a protective pouch. This pouch or balloon may also serve similarly as bias balloon 150 to eliminate respiratory artifacts by filling it with perhaps 0.1 cc of air for making the required measurements.

Figure 9:
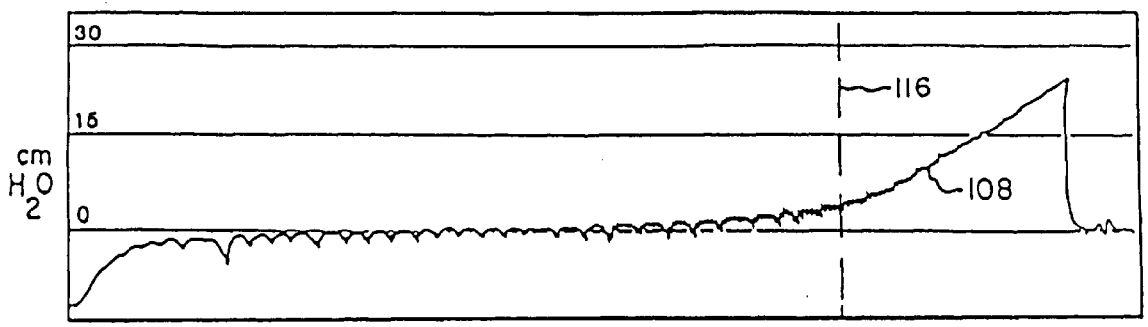
FIG. 9 is a pressure trace of an unfiltered signal of balloon pressure with respiratory and cardiac effected oscillations when the balloon of FIG. 1 is adjacent the left atrium, as the balloon is gradually pressurized.
Figure 10:
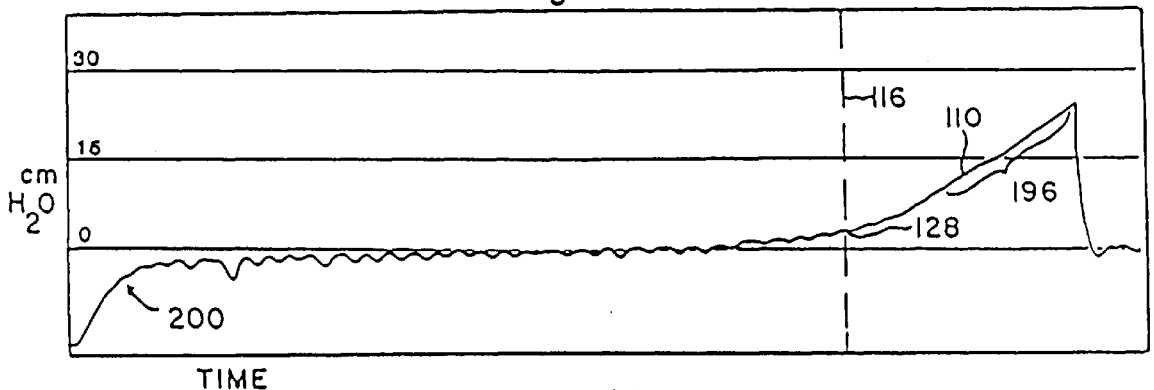
FIG. 10 is a pressure trace of mean balloon pressure for the pressure trace of FIG. 1.
Figure 11:
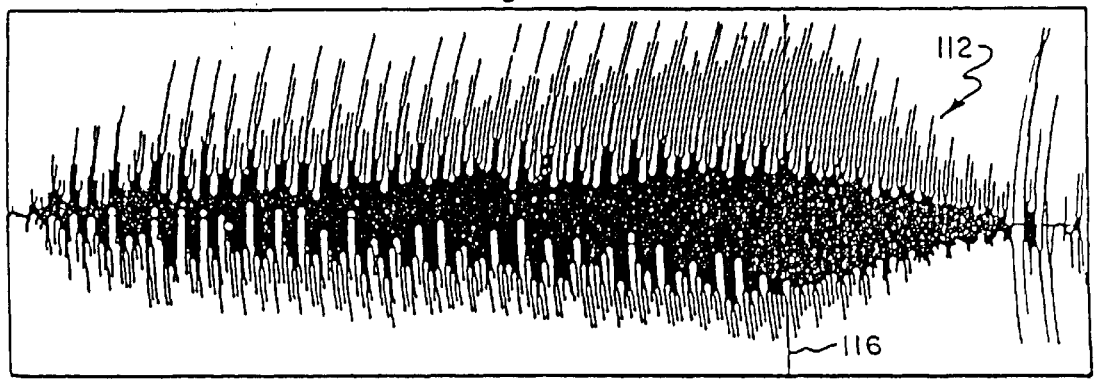
FIG. 11 is a pressure trace of amplified cardiac signal on a steady baseline which signal is derived from the balloon pressure trace of FIG. 9 and covers the same time period as that of FIGS. 9 and 10.

As shown in FIGS. 9 and 10, the low frequency oscillations representative of respiratory artifact decrease in amplitude as the pressure in the balloon 24 increases. In order that the same amplitude of respiratory wave at each point in time may be supplied to both sides of the pressure transducer 68 so that effective cancellation of respiratory artifact may be achieved, balloons 150 and 24 are both connected to gas supply 100 via line 60. Thus, lines 61 and 155 connect line 60 to line 154 for inflation of balloon 150. In order to prevent the cardiac signals from appearing on the bias balloon signal, a suitable low pass filter 157, which may be similar to filter 72, is connected so that line 61 extends from line 60 to input pressure from pressure source 100 to filter 157, and the output of filter 157, with the cardiac waves removed, is transmitted via lines 155 and 154 to balloon 150. In accordance with an alternative embodiment (not shown), two separate gas supplies may be provided for balloons 24 and 150 to prevent signal contamination with suitable pressure transducers and electronic feedback means to automatically maintain the mean pressure in the bias balloon 150 equal to the mean pressure in the sensing balloon 24. In accordance with another alternative embodiment (not shown), two separate gas supplies may be provided with a pressure regulator on the bias balloon side which is referenced to the mean sensing balloon pressure and such that cardiac oscillations are not conducted across the regulator.

It should be understood that other means, for example, analog or digital filtering techniques applied directly to the absolute balloon pressure to remove low frequency artifacts such as from respiration or peristalsis may be used for deriving wave form 112 from the absolute balloon pressure, and such other means are meant to come within the scope of the present invention.

The wave form 112 is thus an oscillating signal of varying amplitude on a steady baseline. These oscillations, derived from absolute balloon pressure, are in response to the driving pressure of the left atrium.

By noting the peak resonant amplitude of the wave form 112 (FIG. 11) and comparing it to the simultaneous mean balloon pressure 110 (FIG. 10), the mean left atrial pressure can be determined. Thus, in accordance with the oscillometric principle, the mean balloon pressure approximates the mean left atrial pressure when the oscillations of wave form 112 are at a peak, i.e., the peak or highest amplitude oscillations in the wave form 112 occur at the time 116 the balloon pressure is equal to mean left atrial pressure. The mean left atrial pressure is thus determined from the example of FIGS. 9 to 12 to be a pressure, illustrated at 128, of about 3 cm water. It should be understood that pressure 128 approximates mean left atrial pressure. To obtain a more precise determination of mean left atrial pressure, the pressure 128 must be adjusted for the effects of heart weight, as discussed hereinafter.

It should be recognized that mean left atrial pressure may alternatively be approximated by reference to the absolute balloon pressure wave form 108. Thus, the relatively small amplitude of the high frequency oscillations on wave form 108 would permit one to estimate the mean balloon pressure from which an estimation of mean left atrial pressure may be obtained.

It should be understood that it is not essential to the present invention that the wave forms in FIGS. 9 to 12 be actually obtained in graph or tracing form. For example, an electronic peak detector may alternatively be used to sense the maximum or peak amplitude, and associated electronics may then determine and display the corresponding mean left atrial pressure in accordance with principles commonly known to those of ordinary skill in the art to which this invention pertains.

The relaxed diameter of the normal adult esophagus is about 2.5 cm. The inflated balloon diameter should be less than this in order to avoid stretching the esophagus since, if this were to happen, not all of the balloon pressure would be applied to the left atrial wall with the result that the balloon pressure at peak oscillation would be higher than the mean left atrial pressure. In addition, if the balloon is too large, its inflation may trigger secondary peristalsis. On the other hand, if the inflated balloon diameter is too small, it will not be able to exert adequate pressure against the left atrium during inflation, nor will it have optimal contact area to optimize pulse transmission. The balloon length should be adequate to provide optimal longitudinal contact with the left atrium and pulmonary veins in which the mean pressure equals mean left atrial pressure, but should not extend too far beyond the left atrium where it could pick up pressure artifacts from the aorta, pulmonary artery, right ventricle, or lower esophageal sphincter. In accordance with the above requirements, for use in adults, the balloon 24 preferably has an inflated diameter, illustrated at 132 in FIG. 2, which is between about 0.8 and 1.5 cm and an inflated length, illustrated at 134 in FIG. 1, which is between about 2 and 4 cm. More preferably, the balloon 24 has an inflated diameter 132 of about 1 cm and an inflated length 134 of about 2 to 4 cm., more preferably, about 2.5 cm, providing a volume of about 2 milliliters. This diameter still allows the vertebral column to serve as an anvil since the esophagus is normally collapsed. For children and neonates the above sizes will be suitably reduced.

Maximum oscillation of balloon pressure may coincidentally occur just before the balloon reaches its full volume after which the balloon pressure may rise very sharply, as indicated at 196 in FIG. 10. Sometimes this sharp rise may obscure the point of maximum balloon oscillation. In order to allow better control of balloon pressure filling for smoother balloon inflation near the point of maximum oscillation, a balloon with an exhaust line for exhausting the balloon outside the body is described in the aforesaid U.S. Pat. No. 5,263,485 for the purpose of slowing such a rapid pressure rise. However, the use of a stepping motor for controlling the balloon filling by a syringe, as previously discussed, may desirably eliminate the need for such an exhaust line.

In certain body positions such as supine and semi-recumbent, the heart weight bears on the esophagus. In such a case the balloon pressure 128 must be adjusted for the effect of heart weight, as hereinafter described, to obtain a more precise determination of mean left atrial pressure. In other body positions such as standing, sitting, lying on the side, or prone, the heart weight might not bear on the esophagus, but this will depend on how the heart is suspended in the chest.

The tissue pressure in the chest (mediastinum) reflects the intrapleural pressure, which is usually subatmospheric at end expiration during regular breathing when an individual is sitting. Esophageal pressure by itself is considered to approximate intrapleural pressure at a point in the esophagus away from the weight of the heart. Mean heart weight may be thought of as a static force, seen best in the supine position, which contributes to the local esophageal pressure immediately beneath the heart. Intrapleural pressure and heart weight are additive. The slope change at point 200 in FIG. 10 is believed to occur when the balloon pressure equals the combined pressure effect of the heart weight and the intrapleural pressure.

The oscillometric theory teaches that a pulsatile structure such as the balloon will resonate maximally when the mean pressure outside the structure equals the mean pressure inside the structure. As the balloon is inflated with air while behind the heart, the pressure in the balloon gradually increases and this pressure increase is transmitted to the adjacent tissues. Given good physical coupling between the balloon and the left atrial wall, the balloon should drive the tissue pressure adjacent to the left atrial wall higher than the mean left atrial pressure. As the tissue pressure adjacent to the left atrium reaches mean left atrial pressure, the tissue should resonate maximally and cause the balloon to resonate as well. However, at the moment that this occurs, the balloon pressure may actually be greater than mean left atrial pressure because the balloon pressure will include the effect of heart weight. To determine the heart weight contribution to balloon pressure, it is necessary to know the intrapleural pressure at the moment 200 that the balloon starts to fill. Based on the intrapleural pressure being believed to be approximately equal to esophageal pressure at some point away from where the heart presses on the esophagus, this pressure may be determined by moving the balloon to this position (perhaps at least about 10 or 11 cm. above the heart), evacuating and then filling it. During filling, there will be an initial slope change similar to slope change 200 which will be approximately the intrapleural pressure. Alternatively, mean esophageal pressure may be determined by use of a second balloon whereby the balloon 24 may be kept adjacent the left atrium. The pressure contribution of the heart weight may be calculated to be the pressure (P1) at the initial slope change 200 as the balloon fills while behind the heart less the pressure (P2) at the initial slope change as the balloon fills while away from the heart. In other words, P1−P2=(pressure due to heart weight+intrapleural pressure)−intrapleural pressure=pressure due to heart weight. Therefore, to obtain a more precise determination of mean left atrial pressure, the pressure contribution by the heart weight is subtracted from the peak balloon oscillation pressure.

The distance between slope changes at points 200 and 128 in a free balloon pressure/volume curve is referred to herein as a plateau. It is believed that, to insure correct balloon placement and proper pressure coupling between left atrium and balloon, the peak balloon oscillation pressure must occur within the time frame of the free balloon pressure/volume plateau. Thus, an on-line comparison of free balloon and esophageal balloon curves may be made to allow recognition of inadequate coupling so that any data obtained thereby can be discarded. The balloon diameter may be increased, such as from perhaps 8 to 9 mm, to obtain adequate coupling when the balloon is properly placed adjacent the left atrium.

Determination of mean left atrial pressure thus requires making balloon pressure measurements in two locations, which is bothersome. However, the determination of a more clinically useful physiologic value, the transmural pressure, may be obtained without moving the balloon from its initial position beside the left atrium. This value is particularly important because it can influence the degree to which fluid will leave the pulmonary capillaries and enter the lung tissue, causing pulmonary edema or "wet lungs." Thus, it allows physicians to more precisely determine when a patient could go into pulmonary edema from heart failure or volume overload, and it also allows an assessment of the effect of positive end expiratory pressure with ventilated patients. Clinicians are not accustomed to using this pressure because heretofore it has not been readily available.

Transmural pressure is equal to the mean left atrial pressure minus the intrapleural pressure which is equal to the peak balloon oscillation pressure−[(pressure due to heart weight+intrapleural pressure)−intrapleural pressure]−intrapleural pressure. Thus, transmural pressure equals peak balloon oscillation pressure−(pressure due to heart weight+intrapleural pressure). As previously discussed, the pressure at slope change point 200 is equal to the pressure due to heart weight plus the intrapleural pressure. Therefore, the transmural pressure is equal to the peak balloon oscillation pressure 128 less the pressure at slope change point 200, and both of these values come from the same balloon position, i.e., adjacent the left atrium. Further, since the balloon need not be moved away from the heart to measure esophageal pressure as an approximation of intrapleural pressure, this eliminates any concerns about the validity of esophageal pressure as a measure of intrapleural pressure, about the optimum position in the esophagus for measuring intrapleural pressure, and about any other factors in or around the esophagus that would distort intrapleural pressure determination.

The method and apparatus of the present invention may be used for providing precise determination of mean left atrial pressure for patients connected to respirators. However, when a patient is connected to a breathing machine which uses positive end expiratory pressure (PEEP), the patient's pulmonary capillary wedge pressure (PCWP) and mean left atrial pressure (MLAP) may be elevated as a result, since all intra-thoracic structures are exposed to varying degrees to this pressure. Since mean esophageal pressure reflects intra-pleural pressure (a good measure of the pressure environment in the chest), the mean esophageal pressure will provide a measure of the effect of PEEP on thoracic structures. Thus, the mean left atrial transmural pressure, as provided by the catheter, provides an excellent means to understand the physiologic and clinical impact of PEEP on the heart and lungs since it takes into account simultaneous pressure changes induced in both the left atrium and the esophagus by the imposition of PEEP.

Without wishing to be bound by theory here or elsewhere in this application, it is believed that the balloon best transmits not only pressures acting on it but also sound when unloaded, i.e., maximum sound energy may penetrate the balloon wall when it is not in tension (when the pressure on opposite sides thereof is balanced). Thus, the amplitude of heart sounds or any other sounds transmitted through the balloon and tubing is believed to be greatest when the mean balloon pressure equals the mean left atrial pressure (including the effect, if any, of heart weight) so that the balloon is unloaded. Accordingly, referring to FIGS. 14 and 15, in accordance with the present invention, the balloon pressure may be measured when the amplitude (intensity) of heart sounds, illustrated at 400, or other sound waves (sound pressure level) transmitted by the balloon 24 and tubing 22 is at a peak as an indication (after adjustment, as previously discussed, for the effect, if any, of heart weight) of mean left atrial pressure. Thus, a condenser-type or other suitable microphone, illustrated at 402, is suitably positioned in a suitable housing 404 in an entrance, illustrated at 414, to the tubing 22 to pick up the heart sounds 400, which may then be filtered with a high pass filter, illustrated at 406 in FIG. 15, to remove extraneous frequencies less than perhaps about 30 Hertz. Alternatively, a band pass filter may be used. Thus, the microphone 402 is in pressure or flow communication with the balloon 24 and tubing 22 for receiving the heart sounds 400 passing along the tubing pathway generally free of interference, and the sounds 400 pass through the wall of the balloon 24 on their way to the microphone 402. The microphone 402 may, for example, be an Archer Electret PC-mount condenser microphone element marketed by Radio Shack, a division of Tandy Corp., of Fort Worth, Tex. under its catalog no. 270-090.

The condenser microphone 402 conventionally comprises a pair of spaced foil diaphragms 408 and 410 with an air space 412 therebetween. Diaphragm 408 extends across and closes the opening to a sound-blocking housing 416 to receive sound waves 400 passing through entrance 414 from tubing 22. The spaced diaphragms 408 and 410 act as a capacitor with vibration of diaphragm 408 relative to diaphragm 410 effecting a changing capacitance. Diaphragm 410 is positioned within the housing 416 so as to be isolated from the sound so as not to vibrate under the influence of the sound waves 400 as does the diaphragm 408.

Typical applications of a condenser microphone require the pressure on the diaphragms to be equalized. Normally, the pressure changes encountered such as barometric pressure changes or other pressure changes are relatively small and slow so that very small holes in the casing 402 and diaphragm 410 need only be provided. These pressure equilibration holes are accordingly sufficiently small that sound passing into the casing has a very low intensity thus not causing a significant bias effect while allowing slow pressure equilibration in response to slow barometric pressure changes or the like.

The pressure changes within the tubing 22 due to balloon inflation are on the order of 5 or 6 cm. water (5000 to 6000 dynes/cm$^2$) which represents a 1000 to 10,000-fold increase over the pressure changes (perhaps 2 dynes/cm$^2$ for the sound of a truck racing its motor or less than 0.2 dynes/cm$^2$ for heart sounds) typically encountered by the microphone, and these pressure changes due to balloon inflation occur very rapidly. If not adequately simultaneously equilibrated, these pressure changes due to balloon inflation may cause collapse of the condenser. In order to achieve the desired pressure equilibration for the large rapid pressure changes encountered in the tubing 22, a pressure equilibration hole, illustrated at 418, is drilled to a diameter of perhaps about 0.020 inch, and pressure equilibration holes, illustrated at 420, of a suitable size such as 0.0225 inch are drilled in diaphragm 410 so that the pressure in air space 412 is also equalized.

While the hole 418 as well as holes 420 are of a suitable size for pressure equilibration, the hole 418 may be so large as to not sufficiently prevent the passage of sound waves 400 undesirably resulting in a bias effect. In order to substantially reduce the intensity of sound waves 400 passing through pressure equilibration hole 418, in accordance with the present invention a low pass filter comprising a length of micro-bore tubing 420 having an inside diameter of about 0.15 inch is suitably connected to the hole 418. The length of the tubing 420 required to provide adequate pressure equilibration to the microphone yet block the passage of sound was found empirically to be about 6 inches. The tubing 420 is desirably composed of a rigid material such as, for example, polypropylene or a fine glass tube, which sound does not penetrate well.

The balloon and heart pressure wave forms may typically have frequencies in the range of 3 to 9 Hz. In contrast, the frequency of the sound waves 400 may be in the range of 30 to 300 Hz. The microphone 402 is tuned by means of the length of tubing 420 to allow the low frequency pressure changes to equilibrate across the body of the microphone 402 while preventing or substantially retarding the much higher sound frequencies from equilibrating. The lower frequency air pressure changes may accordingly be transmitted with fidelity through the length of the tubing 420, while the high frequency heart sounds 400 may be attenuated resulting in a loss of amplitude to perhaps $\frac{1}{5}$ of the original amplitude. Such weakened sound waves passing to the diaphragm 410 should not significantly affect the microphone output. For example, an amplitude of 10 acting on the diaphragm 408 may result in a output amplitude of 8, which is considered to be suitable for obtaining the desired relative sound intensity level to a predetermined base line so that a smooth curve with a pronounced peak may be seen.

Figure 14:
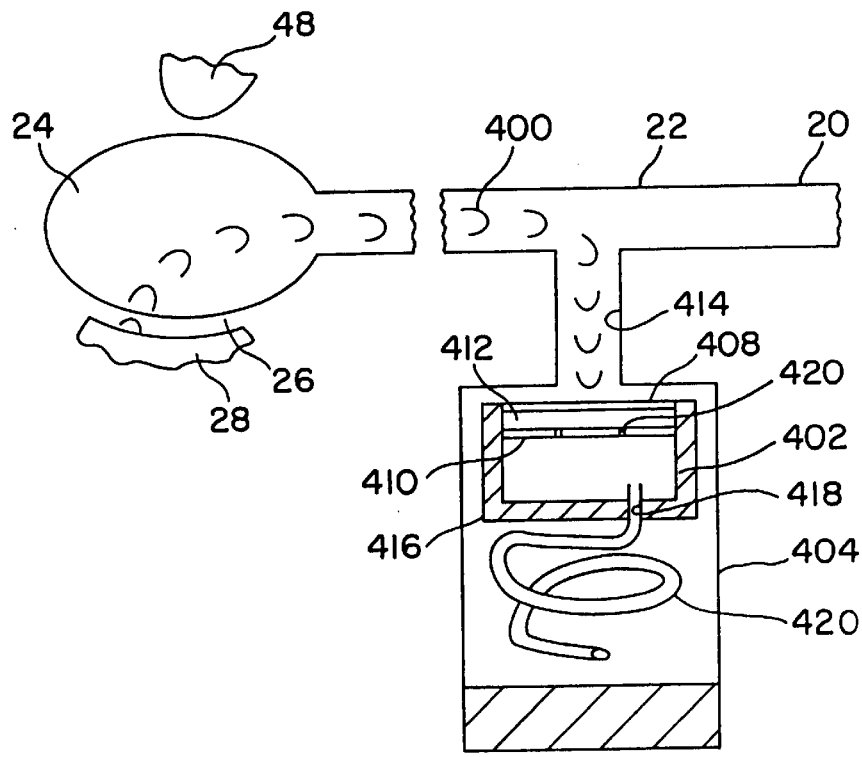
FIG. 14 is a schematic view of apparatus, including the catheter of FIG. 1, in accordance with another embodiment of the present invention.
Figure 15:
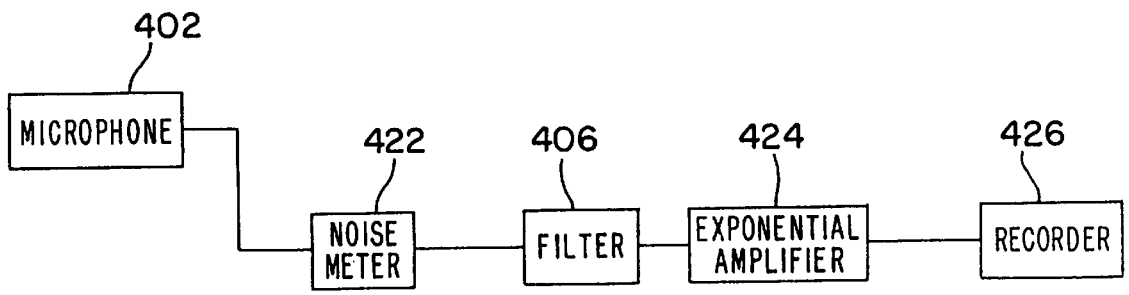
FIG. 15 is a block diagram of electronic components for processing a signal provided by the apparatus of FIG. 14.

For example, for the Radio Shack microphone discussed above, the micro-bore tubing may have a length of perhaps about 6 inches and an inner diameter of perhaps about 0.015 inch. The tubing may, for example, be PE20 low density polyethylene micro-bore tubing manufactured by Clay Adams Intramedic and available from Thomas Scientific of 99 High Hill Road, P.O. Box 99, Swedesboro, N.J. 08085 as featured in the Thomas Scientific catalog of 1991–1992 on page 1364 (catalog no. 9565-S16). The tubing is coiled up as illustrated in FIG. 14 to fit within the housing 404 and installed, for example, by means of a ¼ inch long 25 gage hypodermic stainless steel tube inserted in a 0.02 inch (no. 76 drill) hole in housing 416 and epoxyed thereto to prevent leakage, and the tubing 420 is fit over the stainless steel tube. It should of course be understood that the tubing may be installed in various other ways and other suitable low pass filters may be provided. The tuned microphone thus equilibrates rapidly to the high amplitude low frequency ambient pressure changes but does not equilibrate significantly to very low amplitude, high frequency sound components. Therefore, it can suitably pick up the sound components as desired. This would be the case for dynamic and piezoelectric as well as condenser microphones.

The microphone output may be suitably amplified and recorded for use in obtaining a determination of transmural pressure or other pressure associated with the left atrium. However, in order to obtain a more easily usable representation of the sound, referring to FIG. 15, the microphone output is passed through a suitable noise or sound intensity meter 422 in which a decibel equivalent of the sound output is outputted. This decibel equivalent is then filtered by means of filter 406 which removes respiratory frequencies and the like below about 30 Hz. The filtered signal is then passed through a suitable exponential amplifier 424 where it is exponentially amplified to obtain a more pronounced peak. The filtered and amplified signal may then be recorded on a suitable recorder 426.

Figure 16:
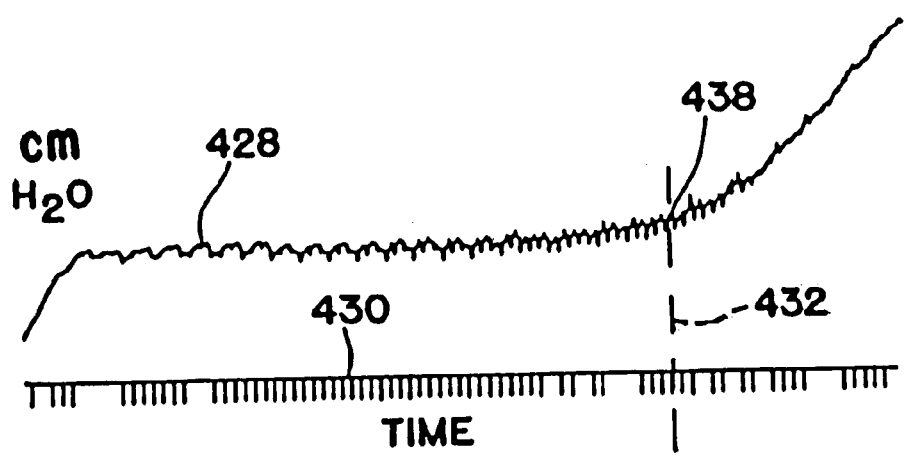
FIG. 16 is a pressure trace similar to that of FIG. 9.
Figure 17:
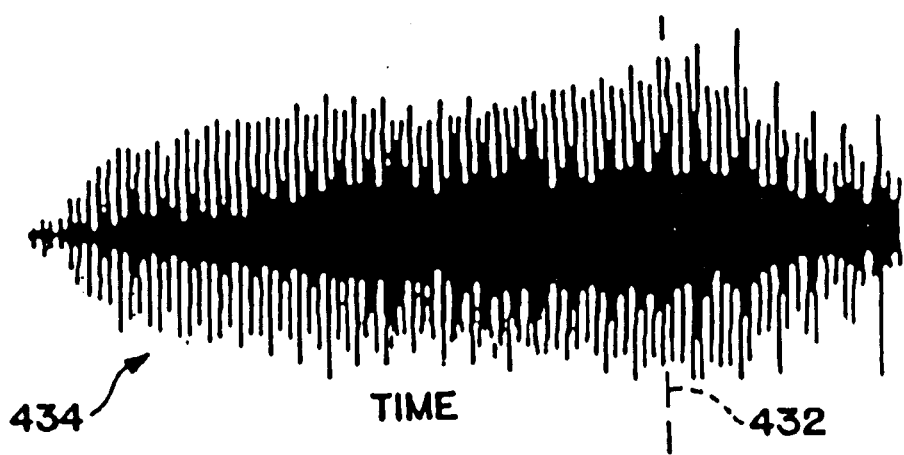
FIG. 17 is a trace of amplified sound output from the apparatus of FIGS. 14 and 15 and covering the same time period as that of FIG. 16.
Figure 18:
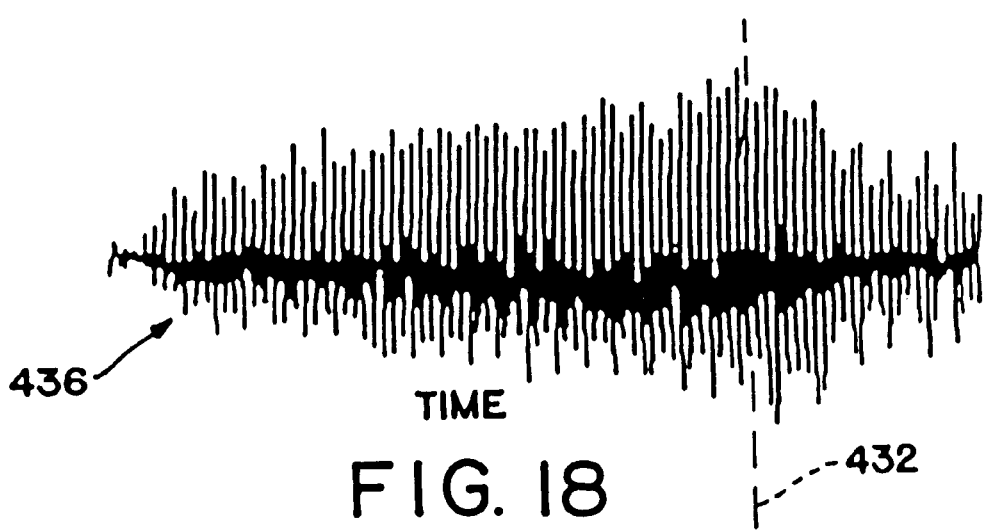
FIG. 18 is a pressure trace similar to that of FIG. 11 which signal is derived from the balloon pressure trace of FIG. 16 and covers the same time period as that of FIGS. 16 and 17.

FIG. 16 shows a tracing 428 similar to that of FIG. 9 of the absolute balloon pressure from the esophageal balloon 24 as it is filled, using a Cobe CDX III transducer. The processes of filling the balloon and measuring balloon pressure may be similar to those described with reference to FIGS. 1 to 13. The tracings in FIGS. 16, 17, and 18 occur over the same period of time, as indicated by time line 430. Vertical line 432 in each of FIGS. 16, 17, and 18 represents the same point in time. Tracing 434 in FIG. 17 is the output from the previously described Electret microphone 402 that has been processed through a 10 to 40 Hz band-pass filter. Tracing 436 in FIG. 18 is a steady baseline oscillometric signal from the balloon 24 which is similarly derived as the signal 112 shown in FIG. 11. FIG. 18 shows that the peak resonant amplitude of the balloon pressure signal occurs at time 432. FIG. 17 shows that the intensity (amplitude) of the sound wave 400 has a peak approximately at time 432. Thus, tracing 436 confirms that a tracing 434 of sound waves transmitted through the balloon 24 may also be used to obtain a determination of mean left atrial pressure or other pressure associated therewith. Thus, tracings 434 and 436 each demonstrate a mean left atrial pressure at point 438, assuming no effect by heart weight.

A method for positioning the balloon 24 adjacent the left atrium may be by the use of an esophageal mapping technique wherein the inflated balloon is lowered to the stomach then slowly pulled up the esophagus. This technique involves locating the second harmonic of the heart rate, i.e., pulse rate and looking for the peak amplitude of the second harmonic as the balloon is slowly pulled up. The balloon is considered to be approximately at the position of the left atrium when the peak amplitude or peak power of the second harmonic is greatest. Since the first harmonic is typically about 1 Hertz, the second harmonic would typically be about 2 Hertz. However, since the heart rate will vary in different individuals, the heart rate and consequently the second harmonic should be known before this technique is used. The second harmonic may be found by using the signal spectrum of the fast Fourier transform, a commonly known mathematical technique, of the balloon pressure signal, using principles commonly known to those of ordinary skill in the art to which this invention pertains. The second harmonic may alternatively be found by other suitable methods such as by use of a digital or analog band pass filter. Thus, by looking for the second harmonic instead of the first harmonic, one may be confident of finding the left atrial component. Of course, the balloon may be positioned by the use of other suitable methods.

During treatment of patients, it may be desirable to insert in the esophagus instruments other than the previously discussed balloon-containing catheter, and it may be necessary to insert such additional instruments to extend beyond the position of the balloon. For example, it may be necessary to insert a naso-gastric tube for providing fluids to or removing fluids from the stomach for feeding or suction. However, by being disposed to lie between the balloon and the esophageal wall, such a tube may undesirably interfere with pressure transmission between the esophageal wall and the balloon for determining mean left atrial pressure.

In order to prevent such an additional instrument from interfering with the balloon-esophagus interface, a nasogastric tube or other elongate means extending beyond the balloon is caused to pass centrally of the balloon so that the balloon surrounds the tube, as discussed more fully in the aforesaid U.S. Pat. No. 5,263,485.

It should be understood that while the present invention has been described in detail herein, the invention can be embodied otherwise without departing from the principles thereof. Such other embodiments are meant to come within the scope of the present invention as defined by the appended claims.

What is claimed is:

1. A method of determining mean left atrial transmural pressure comprising the steps of:
    a. inserting a catheter including a balloon into an esophagus of a subject;
    b. positioning the balloon adjacent the left atrium;
    c. inflating the balloon;
    d. measuring the balloon pressure when the intensity of heart sounds after they are transmitted through the balloon is at a peak; and
    e. adjusting the measured balloon pressure for the effects of heart weight and intrapleural pressure.

2. A method according to claim 1 wherein the step of adjusting the balloon pressure includes subtracting from the measured balloon pressure the balloon pressure at which balloon volume begins to increase greatly relative to the increase in balloon pressure.

3. A method according to claim 1 wherein the step of measuring the balloon pressure comprises measuring the mean balloon pressure when the intensity of heart sounds after they are transmitted through the balloon is at a peak.

4. A method of determining mean left atrial transmural pressure comprising the steps of:
    a. inserting a catheter including a balloon into an esophagus of a subject;
    b. positioning the balloon adjacent the left atrium;
    c. inflating the balloon;
    d. measuring the balloon pressure when the amplitude of balloon pressure oscillations having a frequency greater than about 0.8 Hertz is at a peak; and e. adjusting the measured balloon pressure for the effects of heart weight and intrapleural pressure.

5. A method according to claim 4 wherein the step of measuring the balloon pressure comprises measuring the mean balloon pressure when the amplitude of balloon pressure oscillations having a frequency greater than about 0.8 Hertz is at a peak.

6. A method according to claim 4 wherein the step of adjusting the balloon pressure includes subtracting from the measured balloon pressure the balloon pressure at which balloon volume begins to increase greatly relative to the increase in balloon pressure.

* * * * *